United States Patent [19]

Bugaut et al.

[11] Patent Number: 4,886,517
[45] Date of Patent: Dec. 12, 1989

[54] DYEING COMPOSITION FOR HUMAN HAIR CONTAINING AN AZO DYE

[75] Inventors: Andree Bugaut, Boulogne-Billancourt; Alex Junino, Livry-Gargan; Jean Cotteret, Limay, all of France

[73] Assignee: L'Oreal, Paris, France

[21] Appl. No.: 266,310

[22] Filed: Oct. 31, 1988

Related U.S. Application Data

[63] Continuation of Ser. No. 781,139, Sep. 27, 1985, abandoned.

[30] Foreign Application Priority Data

Oct. 1, 1985 [LU] Luxembourg ............... 85 564

[51] Int. Cl.$^4$ ............... A61K 7/12; C07C 107/06; C09B 29/01; C09B 29/085
[52] U.S. Cl. ............... 8/416; 8/405; 8/408; 8/410; 8/414; 8/415; 8/431; 534/857; 534/887
[58] Field of Search ............... 534/857, 887; 8/410, 8/408, 405, 414, 415, 416

[56] References Cited

U.S. PATENT DOCUMENTS

| | | | |
|---|---|---|---|
| 1,850,155 | 3/1932 | Reddelien et al. ............... | 534/857 |
| 2,691,595 | 10/1954 | Drautz ............... | 106/22 |
| 3,153,564 | 10/1964 | Morgan ............... | 534/857 X |
| 3,164,522 | 1/1965 | Charle et al. ............... | 167/88 |
| 3,617,163 | 11/1971 | Kalopissis ............... | 534/857 |
| 4,226,784 | 10/1988 | Kalopissis ............... | 534/887 |

FOREIGN PATENT DOCUMENTS

| | | | |
|---|---|---|---|
| 610320 | 12/1933 | Fed. Rep. of Germany ...... | 534/857 |
| 1585308 | 12/1969 | France ............... | 534/857 |
| 213567 | 2/1941 | Switzerland ............... | 534/854 |
| 1008858 | 11/1965 | United Kingdom ............... | 8/416 |

OTHER PUBLICATIONS

G. Shulman, Journal of the American Chemical Society, vol. 63, 1941, pp. 3236-3237.

*Primary Examiner*—Floyd D. Higel
*Attorney, Agent, or Firm*—Fleit, Jacobson, Cohn, Price, Holman & Stern

[57] ABSTRACT

The present invention relates to a composition for dyeing keratinic fibres, and human hair in particular, comprising the azo dye of formula:

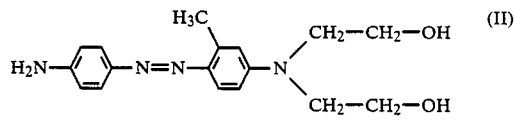

optionally in combination with at least one nitro benzene dye or with at least one aminoanthraquinone dye or with at least one nitro benzene and at least one aminoanthraquinone dye. The azo dye of formula (II) is nonmutagenic, has good solubility properties in the usual dye carriers, and imparts to hair hues which are stable, particularly to washing. The invention also relates to a process for dyeing human hair by direct coloration which comprises applying the dyeing composition defined above onto the hair, leaving it on the hair for 3 to 60 minutes and then rinsing and drying the hair.

25 Claims, No Drawings

DYEING COMPOSITION FOR HUMAN HAIR CONTAINING AN AZO DYE

This application is a continuation of application Ser. No. 781,139, filed Sept. 27, 1985, now abandoned.

The present invention relates to new dyeing compositions for keratinic fibres, containing an azo dye, a new process for preparing this dye, and the use of the said compositions for dyeing keratinic fibres, and in particular human hair.

To dye hair, the expert makes use either of what is known as oxydative dyes or of direct dyes. The former produce shades which give better cover and are more tenacious, but have the disadvantage of not being wholly harmless and requiring an oxidation which is accompanied by hair deterioration. In addition, their very high tenacity and their high affinity for hair entail, in most cases, the appearance of a borderline phenomenon between the ends and half-lengths which are dyed and the undyed roots.

These faults do not make their appearance in the case of direct dyes, and in particular in the case of nitro benzene dyes which are by far the most widely employed in the field of direct dyeing. However, even the latter are not free from disadvantages.

Among other faults, they are criticised as being insufficiently resistant to washing and, in some cases, as having an inadequate affinity for unsensitized natural hair.

To overcome this fault, attempts have been made to combine with nitro benzene dyes some dyes belonging to groups which are compatible with the essential requirements of direct dyeing. From this point of view, the most widely employed dyes are azo dyes and aminoanthraquinone dyes.

The category of aminoanthraquinone dyes contains essentially blue or violet dyes which meet both the required criteria: good affinity for natural hair and good resistance to washing. A typical example of these aminoanthraquinone dyes consists of 1,4,5,8-tetraaminoanthraquinone of formula (III) below, sold under the trade name of "Bleu extra celliton" by BASF.

In the list in the CTFA Cosmetic Ingredient Dictionary, this dye appears under the name "Disperse Blue 1" (Colour Index No. 64,500).

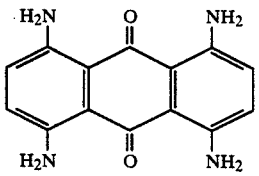

Yellow dyes are essentially to be found among the azo dyes. A typical example of these dyes consists of 4-amino-4'-[N,N-bis($\beta$-hydroxyethyl)amino]phenylazobenzene of formula (I) below:

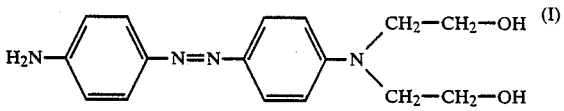

This compound appears in the CTFA Cosmetic Ingredient Dictionary under the name of "Disperse Black 9"; it has no Colour Index number.

The combination of the aminoanthraquinone dye (III) and of the azo dye (I) in dyeing keratinic fibres is described in French Patent 1,585,308.

Although 4-amino-4'-[N,N-bis($\beta$-hydroxyethyl)amino]phenylazobenzene (I) has an improved stability to washing when compared to nitro benzene dyes, it is not wholly satisfactory from a technical standpoint, in particular in respect of its solubility in the usual dye carriers and the fastness of the shades which it enables to be obtained, particularly when employed in combination with aminoanthraquinone dyes.

This same azo dye (I), in addition, is not entirely satisfactory from the point of view of being harmless.

In point of fact, according to the Ames test (Proc. Nat. Acad. USA, vol. 72, No. 12, pages 5135-5139, 1975), it has been found that it was mutagenic to five strains of the Salmonella type in the presence of a S-9 Mix microsomal activator.

The Applicants have consequently investigated other azo dyes which offer improved freedom from hazard, good solubility characteristics in the usual dye carriers, and which produce colours which are stable on hair, particularly to washing.

Among these azo dyes, the compound of formula (II) below:

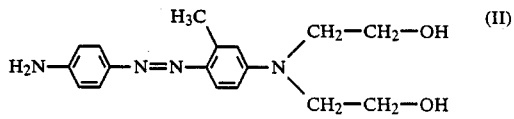

namely 4-amino-2'-methyl-4'-[N,N-bis($\beta$-hydroxyethyl)amino]phenylazobenzene has been found to be of great interest from the standpoint of freedom from hazards, because its non-mutagenicity has been demonstrated.

The compound of formula (II) also has the advantage of having a good solubility in the usual dye carriers. For example, its solubility in 96° ethanol at 25° C. is 5.3%, while under the same conditions the solubility of 4-amino-4'-[N,N-bis($\beta$-hydroxyethyl)amino]phenylazobenzene of formula (I) is only 1.3%.

In addition, the Applicants have found, surprisingly, that in addition to its improved freedom from hazards and its good solubility properties, the dye of formula (II), when employed in combination with an aminoanthraquinone, for example with the compound of formula (III), imparts to natural hair or to hair which has been pretreated, for example sensitized by a permanent wave, an improved dye fastness and especially a better fastness to shampooing.

The present invention consequently relates to a composition for dyeing keratinic fibres, and human hair in particular, containing, in an aqueous, alcoholic or aqueous-alcoholic vehicle, 4-amino-2'-methyl-4'-[N,N-bis($\beta$-hydroxyethyl)amino]phenylazobenzene of formula (II).

In the dye composition according to the invention, the dye of formula (II) may be employed in combination with at least one nitro benzene dye.

According to another embodiment of the present invention, the dye of formula (II) may be employed in combination with at least one aminoanthraquinone dye.

According to a preferred embodiment of the invention, the dye of formula (II) is employed in combination with at least one nitro benzene dye and at least one aminoanthraquinone dye.

Preferably, the nitro benzene dye employed in the dyeing composition of the invention is a blue or violet dye belonging to the category of the nitroparaphenylenediamines having a "hue" according to Munsell of between 2.5 B and 10 RP (see the Apr. 1964 issue of Official Digest, page 375, FIG. 2). However, it may be equally advantageous to also employ, in combination with the azo dye (II), other yellow, orange or red nitrobenzene dyes producing hues which are not included between 2.5 B and 10 RP, and belonging either to the nitroparaphenylenediamine series or to other series of nitrobenzene dyes, for example nitroaminophenols, nitroaminoalkoxybenzenes or nitroaminohydroxyalkoxybenzenes.

The aminoanthraquinone dye is a blue or violet dye having a "hue" which is also between 2.5 B and 10 RP.

The present invention also relates to a dyeing process for keratinic fibres, and human hair in particular, by direct dyeing with the aid of the dye composition described above.

Another subject of the present invention consists of a new process for preparing the compound of formula (II).

Among the blue or violet nitro benzene dyes belonging to the category of the nitroparaphenylenediamines preferably employed according to the invention, mention can be made of the following, without this list being of a restrictive nature:

2-(N-methyl)amino-5-[N,N-bis($\beta$-hydroxyethyl)amino]nitrobenzene;
2-(N-methyl)amino-5-[N-methyl-N-($\beta$-hydroxyethyl)amino]nitrobenzene;
2-(N-$\beta$-hydroxyethyl)amino-5-[N,N-bis($\beta$-hydroxyethyl)amino]nitrobenzene;
2-(N-$\beta$-hydroxyethyl)amino-5-[N-methyl-N-($\beta$-hydroxyethyl)amino]nitrobenzene;
2-(N-$\gamma$-hydroxypropylamino)-5-[N,N-bis($\beta$-hydroxyethyl)amino]nitrobenzene;
2-(N-$\beta$-aminoethylamino)-5-[N,N-bis($\beta$-hydroxyethyl)amino]nitrobenzene;
2-(N-methylamino)-5-[N-methyl-N-($\beta,\gamma$-dihydroxypropyl)amino]nitrobenzene;
2-amino-5-[N,N-bis($\beta$-hydroxyethyl)amino]nitrobenzene; and
2-N-($\beta$-hydroxyethyl)amino-5-[N-($\beta$-hydroxyethyl)amino]nitrobenzene.

Among the nitrobenzene dyes giving hues which are not included between 2.5 B and 10 RP, there may be mentioned, without a restriction being implied:

2-amino-5-N-methylaminonitrobenzene,
2,4-diaminonitrobenzene,
3,4-diaminonitrobenzene,
2,5-diaminonitrobenzene,
3-amino-4-hydroxynitrobenzene,
3-hydroxy-4-aminonitrobenzene,
2-hydroxy-5-aminonitrobenzene,
2-amino-5-hydroxynitrobenzene,
2-amino-3-hydroxynitrobenzene,
2-amino-5-N-($\beta$-hydroxyethyl)aminonitrobenzene,
2-N-($\beta$-hydroxyethyl)amino-5-hydroxynitrobenzene,
3-methoxy-4-N-($\beta$-hydroxyethyl)aminonitrobenzene,
2-N-methylamino-4-($\beta$-hydroxyethyloxy)nitrobenzene,
2-amino-3-methylnitrobenzene,
2-N-($\beta$-hydroxyethyl)amino-5-aminonitrobenzene,
2-amino-4-chloro-5-N-($\beta$-hydroxyethyl)aminonitrobenzene,
2-amino-4-methyl-5-N-($\beta$-hydroxyethyl)aminonitrobenzene,
2-amino-4-methyl-5-N-methylaminonitrobenzene,
2-N-($\beta$-hydroxyethyl)amino-5-methoxynitrobenzene,
2-amino-5-($\beta$-hydroxyethyloxy)nitrobenzene,
2-N-($\beta$-hydroxyethyl)aminonitrobenzene,
3-amino-4-N-($\beta$-hydroxyethyl)aminonitrobenzene,
3-($\beta$-hydroxyethyloxy)-4-N-($\beta$-hydroxyethyl)aminonitrobenzene,
2-N-methylamino-4-($\beta,\gamma$-dihydroxypropyloxy)nitrobenzene,
2-N-($\beta$-hydroxyethyl)amino-5-($\beta$-hydroxyethyloxy)nitrobenzene,
2-N-($\beta$-hydroxyethyl)amino-5-($\beta,\gamma$-dihydroxypropyloxy)nitrobenzene,
3-hydroxy-4-N-($\beta$-hydroxyethyl)aminonitrobenzene,
3-N-($\beta$-hydroxyethyl)amino-4-N-($\beta$-hydroxyethyl)aminonitrobenzene,
2-amino-4-methyl-5-N-($\beta,\gamma$-dihydroxypropyl)aminonitrobenzene,
2-amino-4-methyl-5-hydroxynitrobenzene,
2-N-($\beta$-aminoethyl)amino-4-methoxynitrobenzene,
2-N-($\beta$-aminoethyl)aminonitrobenzene,
2-N-($\beta$-aminoethyl)amino-5-N-($\beta$-hydroxyethyl)aminonitrobenzene,
2-amino-4-methyl-5-N-($\beta$-aminoethyl)aminonitrobenzene, and
2-amino-4-chloro-5-N-($\beta$-aminoethyl)aminonitrobenzene.

Among the blue or violet aminoanthraquinone dyes preferably employed in the dyeing composition according to the invention, mention can be made by way of nonrestrictive examples of:

1,4,5,8-tetraaminoanthraquinone (III),
1-(4'-methylphenyl)amino-4-hydroxyanthraquinone,
1,4-diaminoanthraquinone,
1-N-methylamino-4-N-($\beta$-hydroxyethyl)aminoanthraquinone,
1,4-bis[N-($\beta$-hydroxyethyl)amino]-5,8-dihydroxyanthraquinone,
(4-methylaminoanthraquinonyl)-1-aminopropyltrimethylammonium hydrochloride,
1-amino-4-N-isopropylaminoanthraquinone,
1-N-methylamino-4-($\gamma$-aminopropyl)aminoanthraquinone,
1,4-diamino-5-($\beta$-hydroxyethyl)aminoanthraquinone,
1,4,5-triaminoanthraquinone,
the sodium salt of 1-amino-4-cyclohexylamino-2-anthraquinonesulphonic acid,
the salts of 1-(4'-hydroxyanthraquinonyl)-4-methyl-2-benzenesulphonic acid,
1,4-diamino-5-nitroanthraquinone, and
1-amino-4-N-methylaminoanthraquinone.

The dyeing composition according to the invention contains 0.01 to 4% by weight of 4-amino-2'methyl-4'-[N,N-bis($\beta$-hydroxyethyl)amino]phenylazobenzene of formula (II).

The total concentration of nitro benzene dyes, when they are present, represents 0.01 to 10% of the total weight of the dyeing composition according to the invention. The aminoanthraquinone dye(s) when present, represent(s) 0.01% to 1.0% of the total weight of the dyeing composition according to the invention.

The dyeing composition according to the invention may include water and/or organic solvents which are acceptable in cosmetics as a suitable vehicle, and more particularly alcohols such as ethyl alcohol, isopropyl alcohol, benzyl alcohol and phenylethyl alcohol, or glycols or glycol ethers such as, for example, ethylene glycol and its monomethyl, monoethyl and monobutyl ethers, propylene glycol, butylene glycol, dipropylene glycol, and diethylene glycol alkyl ethers such as, for example, diethylene glycol monoethyl ether or monobutyl ether, in concentrations of between 0.5 and 20% and preferably between 2 and 10% by weight, relative to the total weight of the composition.

Fatty amides, such as the mono- and diethanolamides of acids derived from copra, of lauric acid or of oleic acid, may also be added to the composition according to the invention in concentrations of between 0.05 and 10% by weight.

Anionic, cationic, nonionic or amphoteric surface-active agents or their mixtures may also be added to the composition according to the invention. Preferably, the surfactants are present in the composition according to the invention in a proportion of between 0.1 and 50% by weight and advantageously between 1 and 20% by weight, relative to the total weight of the composition.

Among the surface-active agents, particular mention may be made of the anionic surface-active agents employed alone or mixed, such as especially the alkali metal salts, the magnesium salts, the ammonium salts, the amine salts or the alkanolamine salts of the following compounds:

alkylsulphates, alkyl ether sulphates, optionally ethoxylated alkylamidesulphates, alkylsulphonates, alkylamidesulphonates, γ-olefin sulphonates;

alkylsulphoacetates;

fatty acids such as lauric, myristic, oleic, ricinoleic, palmitic, stearic acids, acids of copra oil or hydrogenated copra oil, and carboxylic acids of polyglycolic ethers, the alkyl radicals of these compounds having a straight chain containing 12 to 18 carbon atoms.

As cationic surface-active agents, more particular mention may be made of fatty amine salts, quaternary ammonium salts such as alkyldimethylbenzylammonium, alkyltrimethylammonium, alkyldimethylhydroxyethylammonium and dimethyldialkylammonium chlorides and bromides, alkylpyridinium salts, and imidazolinium salts. The alkyl groups in the abovementioned quaternary ammonium derivatives are long-chain groups preferably containing between 12 and 18 carbon atoms.

Amine oxides may also be mentioned among these compounds of a cationic character.

Among the amphoteric surface-active agents which may be employed, mention may be made in particular of alkylamino(mono- and di-)propionates, betaines such as alkylbetaines, N-alkyl-sulphobetaines, N-alkylaminobetaines, the alkyl radical containing between 1 and 22 carbon atoms and cycloimidiniums such as alkylimidazolines.

Among the nonionic surfactants which may, if appropriate, be employed in the compositions according to the invention, mention can be made of:

the condensation products of a monoalcohol, an α-diol, an alkylphenol or an amide with glycidol or a glycidol precursor;

compounds corresponding to the formula:

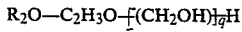

in which $R_2$ denotes an alkyl, alkenyl or alkylaryl radical and q is a statistical value from 1 to 10, these compounds being described more particularly in French Patent 1,477,048, compounds corresponding to the formula:

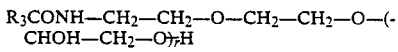

in which $R_3$ denotes a radical or a mixture of straight-chain or branched, saturated or unsaturated aliphatic radicals capable of optionally incorporating one or more hydroxyl groups, containing between 8 and 30 carbon atoms, of natural or synthetic origin and r denotes an integral or decimal number from 1 to 5 and denotes the average degree of condensation, such compounds being described more particularly in French Patent 2,328,763;

alcohols, alkylphenols, fatty amides or fatty acids which are polyethoxylated and contain a straight $C_8$–$C_{18}$ fatty chain;

condensates of ethylene and propylene oxides with fatty alcohols; and polyethoxylated fatty amines.

The thickening products which may be added to the composition according to the invention may advantageously be taken from the group consisting of sodium alginate, gum arabic, guar gum, xanthane gums, cellulose derivatives such as methyl cellulose, hydroxyethyl cellulose, hydroxypropylmethyl cellulose, the sodium salt of carboxymethyl cellulose and acrylic acid polymers.

It is also possible to use inorganic thickening agents such as bentonite.

These thickeners are employed alone or mixed, and are preferably present in a proportion of between 0.5 and 5% by weight relative to the total weight of the composition and, advantageously, between 0.5 and 3% by weight.

The dyeing compositions according to the invention may be formulated at an acid, neutral or alkaline pH, the pH being capable of varying from 4 to 10.5 and preferably from 6 to 10. Among the alkalizing agents which may be employed mention can be made of alkanolamines, alkali metal hydroxides and carbonates, and ammonium hydroxide. Among the acidifying agents which may be employed, mention may be made of lactic acid, acetic acid, tartaric acid, phosphoric acid, hydrochloric and citric acid.

The dyeing compositions may additionally contain various usual adjvants such as antioxidants, perfumes, sequestering agents, film-forming agents and treatment agents, dispersing agents, hair-conditioning agents, preserving agents, opacifiers, and any other adjuvant usually employed in cosmetics.

The dyeing composition according to the invention may be in the various usual forms for hair dyeing, such as thickened or gelled liquids, creams, aerosol foams or any other suitable forms for producing a dye for keratinic fibres.

The dyeing compositions according to the invention are applied to hair for an application time varying between 1 and 60 minutes, preferably between 5 and 45 minutes, which is followed by rinsing, washing if appropriate, rinsing again and drying.

The dyeing compositions according to the invention may be applied to natural or dyed hair, whether permanent-waved or not, or to strongly or slightly bleached, permanent-waved if appropriate, hair. A process for preparing the azo dye of formula (II) employed in the dyeing compositions of the invention is described in the literature [JACS 63, p. 3236 (1941)]. This process employs the reduction, by means of an aqueous solution of sodium hydrogen sulphite, of a compound obtained by the reaction of the diazonium salt of p-nitroaniline with 3-methyl-N,N-bis(β-hydroxyethyl)aniline.

The Applicants have found that the azo dye (II) could be prepared under better conditions by deacetylation with concentrated hydrochloric acid, in the presence or absence of ethanol, of the compound obtained by the reaction of the diazonium salt of p-acetamidoaniline with 3-methyl-N,N-bis(β-hydroxyethyl)aniline.

The process described above makes it possible to avoid the presence of an unidentified impurity, produced concurrently with product (II), when the starting material is para-nitroaniline. This impurity is a by-product formed during the reduction of the NO$_2$ group with the hydrogen sulphite. This impurity, produced in variable quantity depending on the operations, reduces the dyeing power. This process makes it possible to obtain a product which is very pure when examined by chromatography.

The new process for preparing the azo dye of formula (II) according to the invention is illustrated below.

Preparation of
4-amino-2'-methyl-4'-[N,N-bis(β-hydroxyethyl)amino]-phenylazobenzene 1st step Preparation of
4-acetamido-2'-methyl-4'-[N,N-bis(β-hydroxyethyl)amino]phenylazobenzene 0.2 mol (30 g) of p-acetamidoaniline, followed by 34 ml of concentrated hydrochloric acid, are added to 100 ml of water containing 300 g of crushed ice. A solution of 15.2 g of sodium nitrite in 30 ml of water is added to the suspension. The solution obtained in this way is added, after being filtered, to an ice-cold solution of 0.2 mol (39 g) of 3-methyl-N,N-bis(β-hydroxyethyl)aniline in 160 g of water containing 34 ml of concentrated hydrochloric acid. After 30 minutes stirring and making alkaline with a 20% ammonia solution, the product is obtained in the form of crystals.

After filtering, washing with water and alcohol and then drying, the product prepared in this way has a melting point of 220° C.

2nd step

Preparation of
4-amino-2'-methyl-4'-[N,N-bis(β-hydroxyethyl)amino]-phenylazobenzene (II)

A mixture consisting of 0.15 mol (53.4 g) of 4-acetamido-2'-methyl-4'-[N,N-bis(β-hydroxyethyl)amino]phenylazobenzene in 160 ml of concentrated hydrochloric acid containing 320 ml of absolute ethanol saturated with hydrogen chloride gas is heated under reflux.

After this mixture has been heated for 1 hour and cooled, the hydrochloride of the expected product, which has precipitated, is filtered off and then washed with 96° alcohol.

The hydrochloride is dissolved in iced water. After neutralization with ammonia the expected product is precipitated. The product, obtained after filtering, washing with water and then with ethanol, is recrystallized from acetonitrile or alcohol. It melts at 151° C.

Analysis of the product obtained gives the following results:

| ANALYSIS | CALCULATED FOR C$_{17}$H$_{22}$N$_4$O$_2$ | FOUND |
|---|---|---|
| C | 64.97 | 64.95 |
| H | 7.01 | 7.10 |
| N | 17.83 | 17.96 |
| O | 10.19 | 10.30 |

To illustrate the invention better a description will now be given, by way of purely illustrative, nonrestrictive examples, of several embodiments of a dyeing composition according to the invention.

EXAMPLE 1

The following dyeing mixture is prepared:

| | |
|---|---|
| 4-amino-2'-methyl-4'-[N,N—bis(β-hydroxyethyl)amino]phenylazobenzene | 0.8 g |
| 2-butoxyethanol | 10 g |
| 20% weight strength monoethanolamine | 1.5 g |
| Cellosize WPO 3 H (Union Carbide) (hydroxyethyl cellulose) | 2 g |
| ammonium laurylsulphate | 5 g |
| water q.s. | 100 g |
| pH: 9.3 | |

This mixture, applied to hair for 25 minutes at 28° C. gives it, after shampooing and rinsing, a colour:
on white-bleached hair: 2.5 Y 7/8 according to the Munsell notation
on 90% naturally grey hair: 10 YR 7/14 according to the Munsell notation.

EXAMPLE 2

The following dyeing mixture is prepared:

| | |
|---|---|
| 4-amino-2'-methyl-4'-[N,N—bis(β-hydroxyethyl)amino]phenylazobenzene (II) | 0.05 g |
| Bleu extra celliton BASF (III) | 0.10 g |
| Lauric acid | 1 g |
| oleyldiethanolamine | 3 g |
| 2-butoxyethanol | 5 g |
| Ethomeen HT60 (AKZO) | 3.5 g |
| Cellosize WPO 3 H (Union Carbide) | 2 g |
| 2-amino-2-methyl-1-propanol q.s. pH | 9.5 |
| water | 100 g |

This mixture, applied to hair for 20 minutes, gives it, after shampooing and rinsing, a colour:
on natural hair: 8.2 GY 6.6/2.4 according the Munsell notation
on permanent-waved hair: 4 G 5.6/3.6 according to the Munsell notation.

EXAMPLE 3

The following dyeing mixture is prepared:

| | |
|---|---|
| 4-amino-2'-methyl-4'-[N,N—bis(β-hydroxyethyl)amino]phenylazobenzene (II) | 0.05 g |
| Bleu extra celliton BASF (III) | 0.10 g |
| 2-N—(β-hydroxyethyl)amino-5-N,N—bis(β-hydroxyethyl)aminobitrobenzene | 0.10 g |
| lauric acid | 1 g |
| oleyldiethanolamine | 3 g |
| 2-butoxyethanol | 5 g |
| Ethomeen HT 60 (AKZO) | 3.5 g |
| Cellosize WPO 3H (Union Carbide) | 2 g |
| 2-amino-2-methyl-1-propanol q.s. pH 9.5 | |

| | |
|---|---|
| water q.s. | 100 g |

This composition is applied to hair. After 20 minutes' application, rinsing and drying, the hair is of an ash-blond colour.

EXAMPLE 4

The following dyeing composition is prepared:

| | |
|---|---|
| 4-amino-2'-methyl-4'-[N,N—bis($\beta$-hydroxyethyl)amino]phenylazobenzene (II) | 0.2 g |
| 2-N—($\beta$-hydroxyethyl)amino-5-hydroxynitrobenzene | 0.4 g |
| 2-amino-5-hydroxynitrobenzene | 0.4 g |
| lauric acid | 1 g |
| oleyldiethanolamine | 3 g |
| 2-butoxyethanol | 5 g |
| Ethomeen HT 60 (AKZO) | 3.5 g |
| Cellosize WPO 3 H (Union Carbide) | 2 g |
| 2-amino-2-methyl-1-propanol q.s. pH 9.5 | |
| water q.s. | 100 g |

This composition is applied to brown hair. After 20 minutes' application, rinsing and drying, the hair has an intense coppery hue.

EXAMPLE 5

The following dyeing composition is prepared:

| | |
|---|---|
| 4-amino-2'-methyl-4'-[N,N—bis($\beta$-hydroxyethyl)amino]phenylazobenzene (II) | 0.028 g |
| Bleu extra celliton (BASF) (III) | 0.006 g |
| 2-N—methylamino-5-[N—methyl-N—($\beta$-hydroxyethyl)amino]nitrobenzene | 0.16 g |
| 2-N—methylamino-4-($\beta$-hydroxyethyloxy)nitrobenzene | 0.1 g |
| lauric acid | 1 g |
| oleyldiethanolamine | 3 g |
| 2-butoxyethanol | 5 g |
| Ethomeen HT 60 (AKZO) | 3.5 g |
| Cellosize WPO 3 H (Union Carbide) | 2 g |
| 2-amino-2-methyl-1-propanol q.s. pH 9.5 | |
| water q.s | 100 g |

This thickened liquid is applied to sun-bleached blond hair. After 20 minutes' application the hair is rinsed and dried and then is of a revived and natural blond colour.

EXAMPLE 6

The following dyeing composition is prepared:

| | |
|---|---|
| 4-amino-2'-methyl-4'-[N,N—bis($\beta$-hydroxyethyl)amino]phenylazobenzene (II) | 0.14 g |
| Bleu extra celliton (BASF) (III) | 0.03 g |
| 2-N—methylamino-5-[N,N—bis($\beta$-hydroxyethyl)amino]nitrobenzene | 0.55 g |
| 2-N—methylamino-4-($\beta$-hydroxyethyloxy)nitrobenzene | 0.11 g |
| 3-methoxy-4-N—($\beta$-hydroxyethyl)aminonitrobenzene | 0.09 g |
| 2-N—($\beta$-hydroxyethyl)amino-5-hydroxynitrobenzene | 0.2 g |
| 2-amino-5-hydroxynitrobenzene | 0.04 g |
| 2-amino-5-N—methylaminonitrobenzene | 0.05 g |
| lauric acid | 1 g |
| oleyldiethanolamine | 3 g |
| 2-butoxyethanol | 5 g |
| Ethomeen HT 60 (AKZO) | 3.5 g |
| Cellosize WPO 3 H (Union Carbide) | 2 g |
| 2-amino-2-methyl-1-propanol q.s. pH 9.5 | |
| water q.s. | 100 g |

This composition is applied for 20 minutes to brown hair. After rinsing and drying, a light brown hue is obtained.

EXAMPLE 7

The following dyeing composition is prepared:

| | |
|---|---|
| 4-amino-2'-methyl-4'-[N,N—bis($\beta$-hydroxyethyl)amino]phenylazobenzene (II) | 0.47 g |
| Blue extra Celliton (BASF) (III) | 0.07 g |
| 2-N—methylamino-5-[N—methyl-N—($\beta$-hydroxyethyl)amino]nitrobenzene | 0.40 g |
| 2-N—methylamino-4-($\beta$-hydroxyethyloxy)nitrobenzene | 0.11 g |
| 3-methoxy-4-[N—($\beta$-hydroxyethyl)amino]nitrobenzene | 0.05 g |
| 2-N—($\beta$-hydroxyethyl)amino-5-hydroxynitrobenzene | 0.017 g |
| lauric acid | 1 g |
| oleyldiethanolamine | 3 g |
| 2-butoxyethanol | 5 g |
| Ethomeen HT 60 (AKZO) | 3.5 g |
| Cellosize WPO 3 H (Union Carbide) | 2 g |
| 2-amino-2-methyl-1-propanol q.s. pH 9.5 | |
| water q.s. | 100 g |

This formulation forms a thickened liquid which is applied to light brown hair for 20 minutes. The hair is rinsed and dried and is then dyed with a light golden brown hue.

We claim:

1. Composition for dyeing human hair, which comprises, in an aqueous, alcoholic or aqueousalcoholic carrier, a tinctorially effective amount of 4-amino-2'-methyl-4'-[N,N-bis($\beta$-hydroxyethyl)amino]phenylazobenzene of formula:

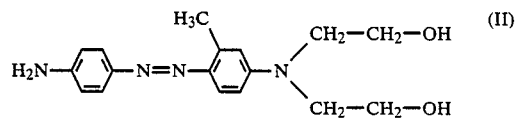

2. Composition according to claim 1, which contains the compound of formula (II) in combination with at least one nitro benzene dye.

3. Composition according to claim 1, which contains the compound of formula (II) in combination with at least one aminoanthraquinone dye.

4. Composition according to claim 1, which contains the compound of formula (II) in combination with at least one nitro benzene dye and at least one aminoanthraquinone dye.

5. Composition according to claim 2, wherein the nitro benzene dye is a blue or violet nitroparaphenylenediamine dye having a Munsell hue of between 2.5 B and 10 RP.

6. Composition according to claim 3, wherein the aminoanthraquinone dye is a blue or violet dye having a Munsell hue of between 2.5 B and 10 RP.

7. Compositions according to claim 5 wherein said nitro benzene dye is a nitroparaphenylenediamine selected from the group consisting of:
2-(N-methyl)amino-5-[N,N-bis($\beta$-hydroxyethyl)amino]nitrobenzene;

2-(N-methyl)amino-5-[N-methyl-N-(β-hydroxyethyl-
)amino]nitrobenzene;
2-(N-hydroxyethyl)amino-5-[N,N-bis(β-hydroxyethyl-
)amino]nitrobenzene;
2-(N-β-hydroxyethyl)amino-5-[N-methyl-N-(β-
hydroxyethyl)-amino]nitrobenzene;
2-(N-γ-hydroxypropyl)amino-5-[N,N-bis(β-hydroxye-
thyl)amino]nitrobenzene;
2-(N-β-aminoethyl)amino-5-[N,N-bis(β-hydroxyethyl-
)amino]nitrobenzene;
2-(N-methylamino)-5-[N-methyl-N-(β,γ-dihydroxy-
propyl)amino]nitrobenzene;
2-amino-5-[N,N-bis(β-hydroxyethyl)amino]nitroben-
zene; and
2-N-(β-hydroxyethyl)amino-5-[N-(β-hydroxyethyl-
)amino]nitrobenzene.

8. Composition according to claim 6, which contains an aminoanthraquinone dye from the group consisting of:
1,4,5,8-tetraaminoanthraquinone (III),
1-(4'-methylphenyl)amino-4-hydroxyanthraquinone,
1,4-diaminoanthraquinone,
1-N-methylamino-4-N-(β-hydroxyethyl)aminoan-
thraquinone,
1,4-bis[N-(β-hydroxyethyl)amino]-5,8-dihydroxyan-
thraquinone,
(4-methylaminoanthraquinonyl)-1-aminopropyltrime-
thylammonium hydrochloride,
1-amino-4-N-isopropylaminoanthraquinone,
1-N-methylamino-4-(γ-aminopropyl)aminoanthraqui-
none,
1,4-diamino-5-(β-hydroxyethyl)aminoanthraquinone,
1,4,5-triaminoanthraquinone,
the sodium salt of 1-amino-4-cyclohexylamino-2-
anthraquinonesulphonic acid,
the salts of 1-(4'-hydroxyanthraquinonyl)-4-methyl-2-
benzenesulphonic acid,
1,4-diamino-5-nitroanthraquinone, and
1-amino-4-N-methylaminoanthraquinone.

9. Composition according to claim 2, which contains at least one yellow, orange or red nitro benzene dye producing a Munsell hue not included between 2.5 B and 10 RP, said nitro benzene dye being selected from the group consisting of nitroparaphenylenediamines, nitroaminophenols, nitroaminoalkoxybenzenes and nitroaminohydroxyalkoxybenzenes.

10. Composition according to claim 1, which contains 0.01 to 4% by weight of the compound of formula (II).

11. Composition according to claim 2 which contains 0.01 to 10% by weight of at least one nitro benzene dye.

12. Composition according to claim 3, which contains 0.01 to 1.0% by weight of at least one aminoanthraquinone dye.

13. Composition according to claim 1, which contains organic solvents selected from the group consisting of alcohols, glycols and glycol ethers, in concentration of between 0.5 and 20% by weight, relative to the total weight of the composition, said alcohols being selected from the group consisting of ethyl alcohol, isopropyl alcohol, benzyl alcohol and phenylethyl alcohol.

14. Composition according to claim 1, which contains fatty amides selected from the group consisting of the mono- and diethanolamides of acids derived from copra, of lauric acid and of oleic acid, in concentrations between 0.05 and 10% by weight relative to the total weight of the composition.

15. A composition according to claim 1, which contains anionic, cationic, nonionic or amphoteric surface-active agents or their mixtures, in concentrations between 0.1 and 50% by weight, relative to the total weight of the composition.

16. Composition according to claim 1, which contains thickeners in concentrations of between 0.5 and 5% by weight, relative to the total weight of the composition.

17. Composition according to claim 1, which additionally contains usual adjuvants selected from the group consisting of antioxidants, perfumes, sequestering agents, film-forming agents, treatment agents, dispersing agents, hair-conditioning agents, preserving agents, and opacifiers.

18. Composition according to claim 1, which has a pH between 4 and 10.5.

19. Process for dyeing human hair, by direct dyeing, wherein the dyeing composition according to claim 1 is applied and that after an application time of 3 to 60 minutes, the hair is rinsed and then dried.

20. The composition of claim 4 wherein the nitrobenzene dye is a blue or violet nitroparaphenylenediamine dye having a Munsell hue of between 2.5 B and 10 RP.

21. The composition of claim 4 wherein the aminoanthraquinone dye is a blue or violet dye having a Munsell hue of between 2.5 B and 10 RP.

22. The composition of claim 4 which contains 0.01 to 10% by weight of at least one nitrobenzene dye.

23. The composition of claim 4 which contains 0.01 to 1.0% by weight of at least one aminoanthraquinone dye.

24. Composition according to claim 1, which contains the compound of formula (II) in combination with 1,4,5,8-tetraaminoanthraquinone (III).

25. Composition according to claim 1, which contains the compound of formula (II) in combination with 1,4,5,8-tetraaminoanthraquinone (III) and at least one nitro benzene dye.

* * * * *